July 31, 1962 J. H. URABEC Plant Pat. 2,159
CAMELLIA PLANT
Filed April 4, 1961
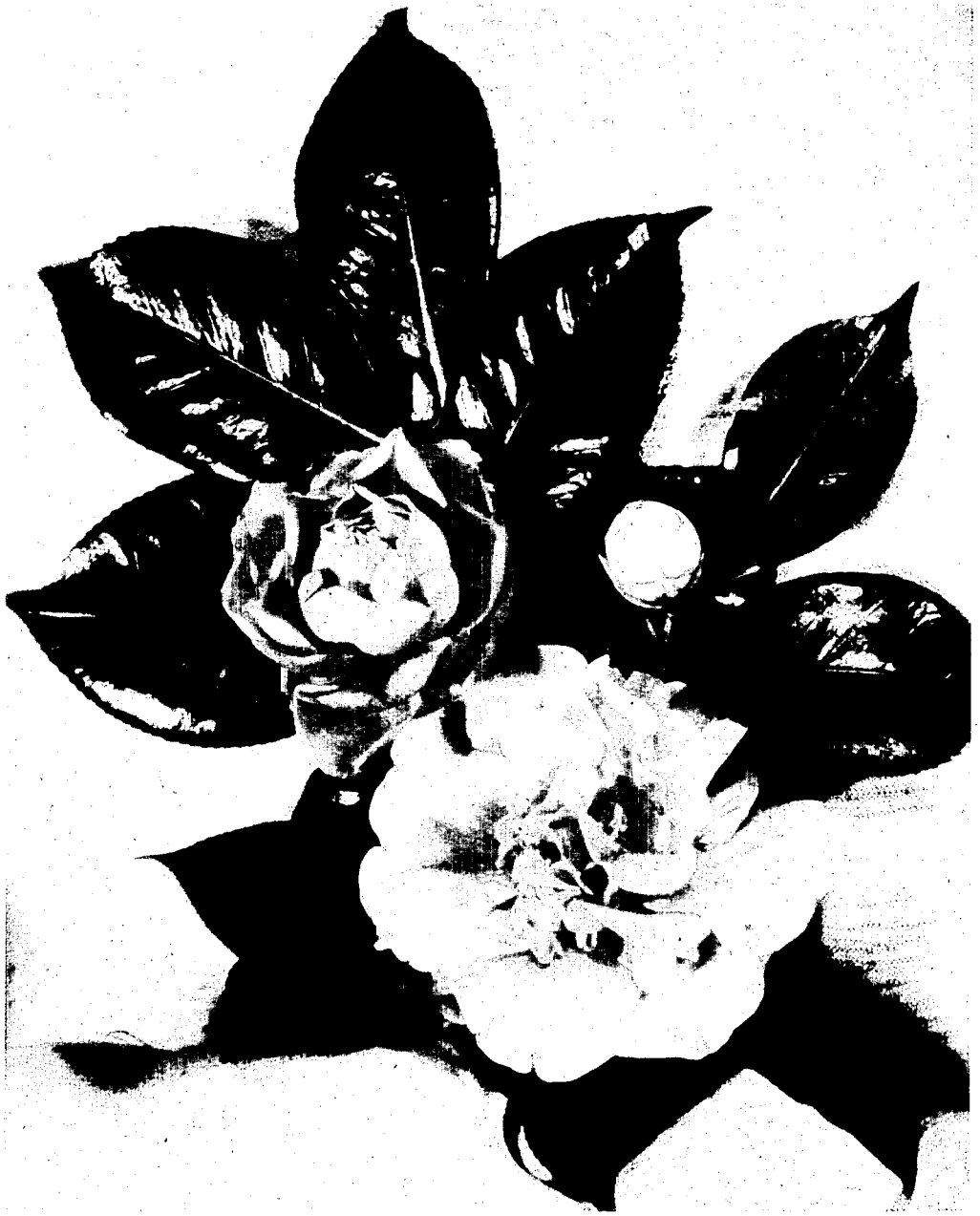
INVENTOR
John H. Urabec
BY Robb & Robb
ATTORNEYS United States Patent Office Plant Pat. 2,159
Patented July 31, 1962

2,159
CAMELLIA PLANT

John H. Urabec, 2555 Hill Drive, Los Angeles, Calif.

Filed Apr. 4, 1961, Ser. No. 100,767
1 Claim. (Cl. 47—60)

The present invention relates to a new and distinct variety of camellia plant of the japonica type, which was originated by me as a selected seedling of unknown parentage.

For some years, I have been growing camellia plants on my cultivated property at Los Angeles, California, and have been gathering seed from such plants, planted the seeds in special beds, and grown seedlings therefrom for the purpose of seeking new and improved varieties. The present seedling is one of those which I planted along with other seedlings of various parentage, and because this particular seedling showed that it possessed unique and desirable characteristics when it first bloomed, it was carefully preserved and observed over a period of several years. Still later, it was asexually reproduced by me by grafting, as performed on my property aforesaid at Los Angeles. Continued observations of the original seedling, as well as the progeny thereof, have conclusively established that the variety is endowed with a unique combination of characteristics which are fixed and established, and capable of being transmitted through succeeding propagations.

The following characteristics are outstanding in the new variety and distinguish it from all other varieties of which I am aware:

(1) Exceptionally large flower size, ranging from about 12.5 to about 17.75 centimeters in diameter when fully open;

(2) Attractive, loosely arranged flowers of incomplete double form with large and small inner petals; and (3) A distinctive and attractive Rhodamine Pink general color tonality of the flowers which tends to deepen in color with age.

The accompanying drawing shows typical specimens of the flowers and foliage of my new variety in different stages of development and as depicted in color as nearly true as it is reasonably possible to make the same in a color illustration of this character.

The following is a detailed description of my new camellia variety, with color terminology in accordance with the Horticultural Colour Chart of the Royal Horticultural Society, except where general color terms of ordinary dictionary significance are obvious:

Parentage: A seedling of unknown parentage.

Propagation: Holds its distinguishing characteristics through succeeding propagations by grafting.

Blooming habit: Midseason; begins about January 1 in southern California.

Bud:

*Size.*—Large.

*Form.*—Globular; rather short with flat top.

*Sepals.*—Usually 3 petaloid sepals up to 4.5 cm. long and 4.2 cm. wide. Color—similar to petal color with greenish-white apices.

*Calyx.*—Up to 5 cm. across; flat. Color: outer segments—brown; inner segments—pinkish, with brown margins.

Bloom:

*Size (when fully open).*—Large; from about 12.5 to about 17.75 cm. in diameter.

*Borne.*—Singly; on stems of normal strength.

*Form.*—Loosely arranged; irregular; double.

*Petalage.*—Usually about 10 guard petals and from 10 to 12 folded, undulated upright petals commonly known as "rabbit-ear" petals; balance of the center of the flower consisting of a great number of petaloids intermixed with stamens, and arranged in large, dense fascicles, in some of the flowers, carrying from 20 to 30 petaloids and united halfway.

*Color.*—Basic color Rhodamine Pink, Plate 527/2, with veining of Rhodamine Pink, Plate 527/1, with margins and petaloids fading to Rhodamine Pink, Plate 527/3; flower tends to deepen in color with age.

Petals:

*Texture.*—Guard petals of medium substance.

*Shape.*—Obovate; slightly recurved; slightly undulated; up to 7 cm. long and 5 cm. wide; apices slightly notched; stout hafts; smooth margins.

*Lasting quality.*—On the plant—excellent. As cut flower—excellent.

Genital organs:

*Stamens, anthers.*—Small. Color—yellow.

*Stamens, filaments.*—Medium length. Color—white.

*Pollen.*—Color—yellow.

Fruit:

*Fertility.*—Fertile with its own pollen.

*Form.*—Round.

*Aspect.*—Smooth.

*Color (at maturity).*—Green.

Plant:

*Form.*—Bush.

*Growth.*—Vigorous; upright; medium height; free-flowering.

*Foliage.*—Form—elliptic. Texture—medium. Size—large (from about 7.5 cm. to 9.5 cm. long and from about 4.5 cm. to 5.5 cm. wide). Margins—crenate. Apices—from medium to long pointed. Petioles—medium stout; up to 1 cm. long. Venation—perceptible on both sides but slightly more prominent on upper surface than on under surface. Color: new foliage—dark green; dull on upper side and somewhat lighter green and semi-glossy on the under side; old foliage—green.

Wood:

*New wood.*—Color—green.

*Old wood.*—Color—from brown to grey.

I claim:

A new and distinct variety of camellia plant, substantially as herein shown and described, characterized particularly as to novelty by the unique combination of an exceptionally large flower size, attractive, loosely arranged flowers of incomplete double form with large and small inner petals and a distinctive and attractive Rhodamine Pink general color tonality of the flowers which tends to deepen in color with age.

No references cited.